United States Patent [19]

Blake, III

[11] Patent Number: 4,532,925

[45] Date of Patent: Aug. 6, 1985

[54] LIGATOR DEVICE

[75] Inventor: Joseph W. Blake, III, 88 Main St., New Canaan, Conn. 06840

[73] Assignees: Joseph W. Blake, III, New Canaan, Conn.; Jack W. Kaufman, Merrick, N.Y.

[21] Appl. No.: 313,341

[22] Filed: Oct. 20, 1981

Related U.S. Application Data

[63] Continuation-in-part of Ser. No. 63,268, Aug. 2, 1979, Pat. No. 4,296,751.

[51] Int. Cl.³ .............................................. A61B 17/12
[52] U.S. Cl. ................................. 128/325; 29/243.56; 72/410; 227/DIG. 1
[58] Field of Search ............... 128/321, 325, 326, 322, 128/334 R; 433/159; 81/349; 29/243.56; 72/410; 227/DIG. 1, 19

[56] References Cited

U.S. PATENT DOCUMENTS

| Re. 27,146 | 6/1971 | Rozmus | 81/349 X |
|---|---|---|---|
| 600,504 | 3/1898 | Autio | 81/349 |
| 1,498,488 | 6/1924 | Stallings | 81/309 |
| 2,455,833 | 12/1948 | Trombetta | 128/326 |
| 3,047,874 | 8/1962 | Kelsey | 72/410 |
| 3,230,758 | 1/1966 | Klingler | 72/410 |
| 3,646,801 | 3/1972 | Caroli | 128/334 R X |
| 3,844,289 | 10/1974 | Noiles | 128/334 R |
| 4,166,466 | 9/1979 | Jarvik | 128/325 |
| 4,246,903 | 1/1981 | Larkin | 128/325 |

FOREIGN PATENT DOCUMENTS

| 627970 | 3/1936 | Fed. Rep. of Germany | 128/325 |
|---|---|---|---|
| 881030 | 6/1953 | Fed. Rep. of Germany | 81/349 |

Primary Examiner—Michael H. Thaler
Attorney, Agent, or Firm—Charles J. Knuth; Peter C. Richardson; Harold W. Ordway

[57] ABSTRACT

A ligator device has handles which are linked to a center slide to make the same move rearwardly when the handles are squeezed together. A pair of jaws surround the front of the slide top and bottom and are connected to it so as to open when the handles are released and close when the handles are squeezed. The forward ends of the jaws carry anvils which, when closed, squeeze ligating clips shut which are supplied from a magazine.

1 Claim, 5 Drawing Figures

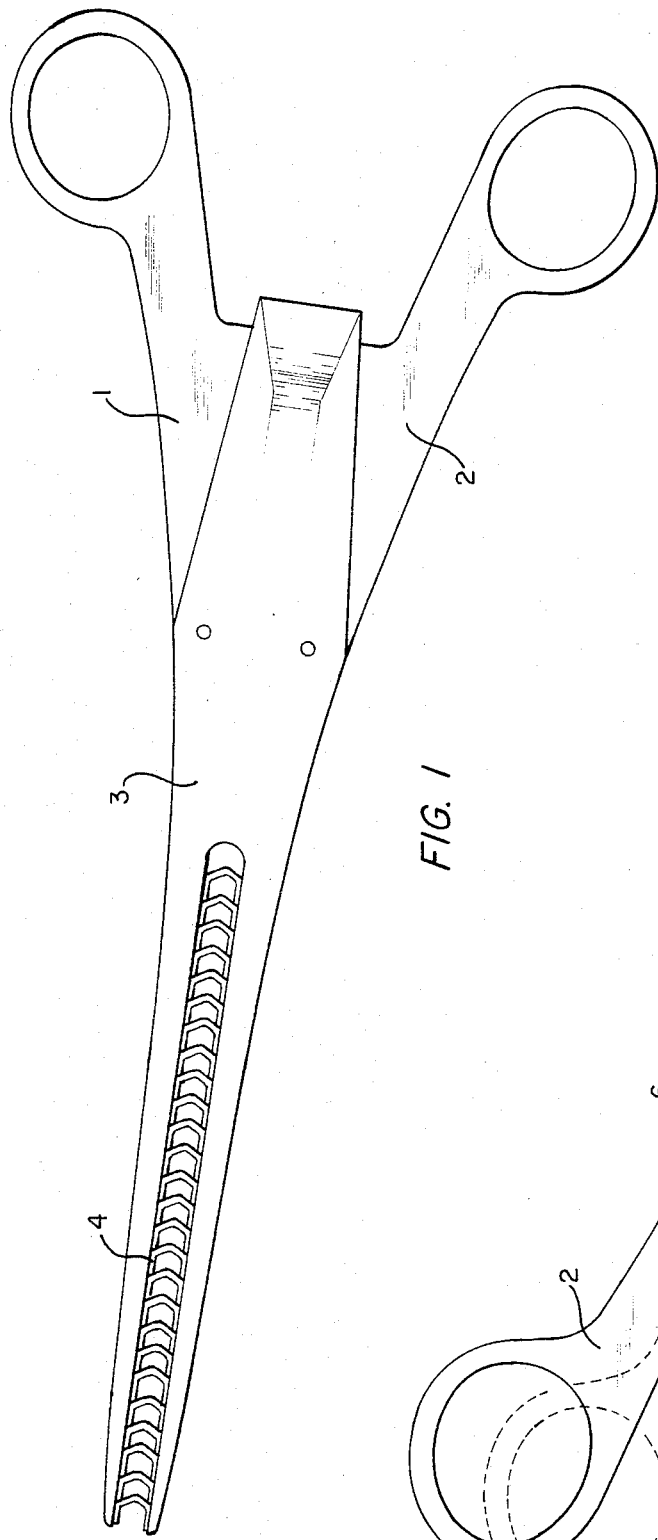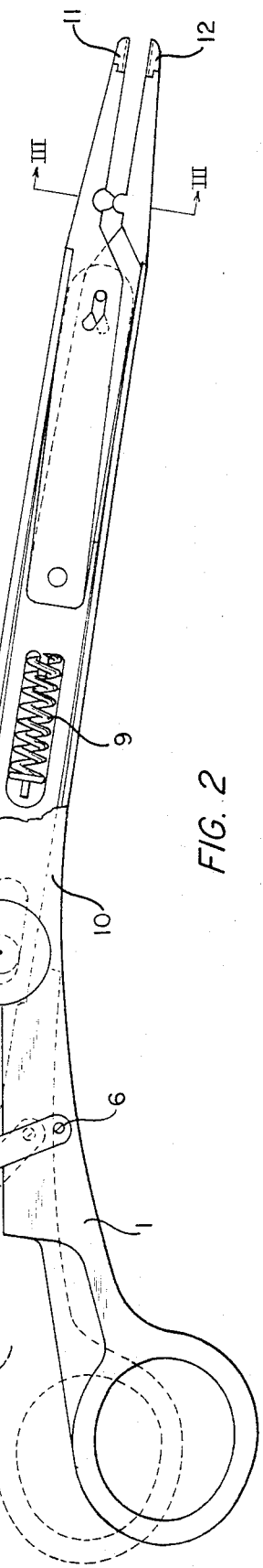

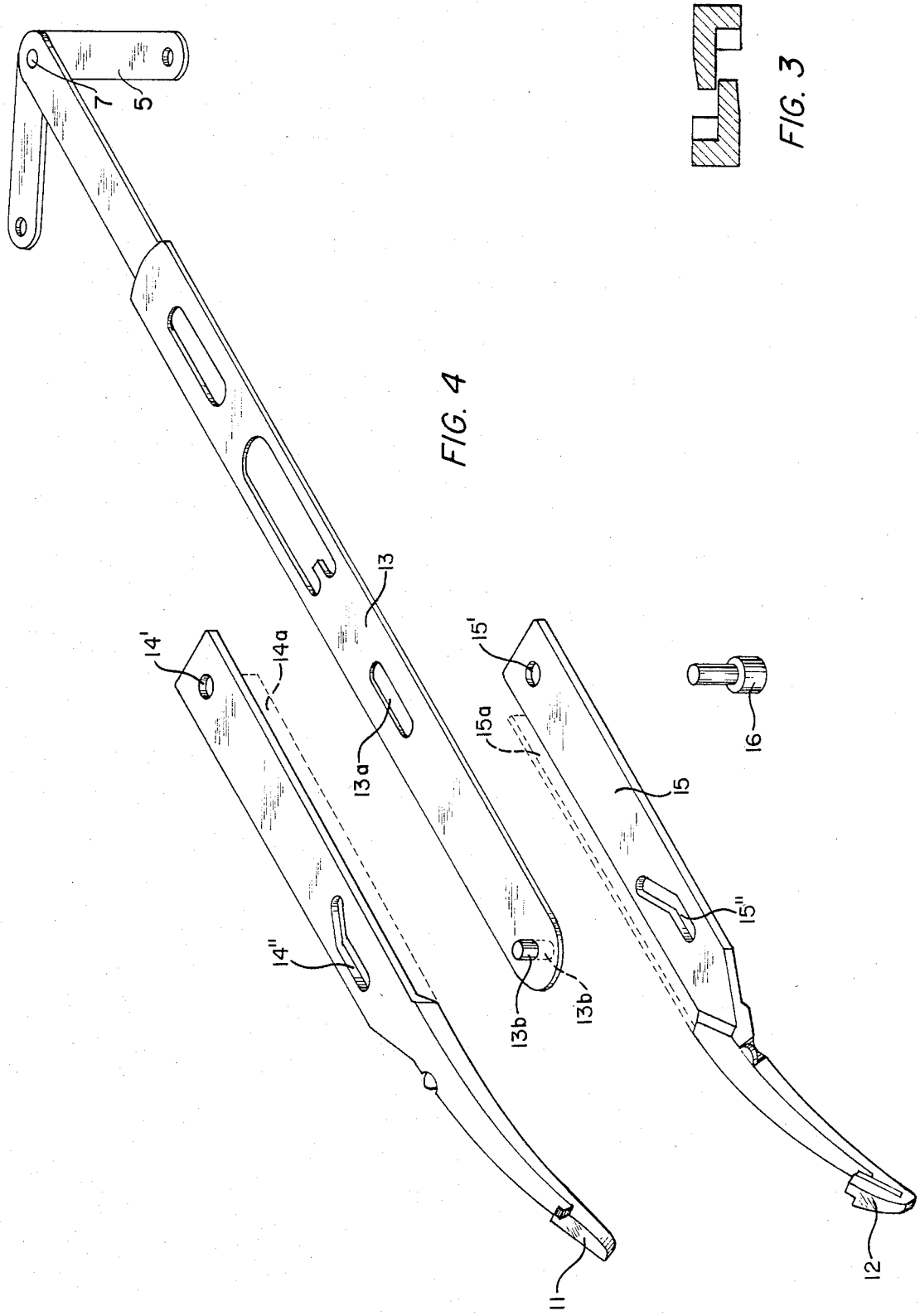

LIGATOR DEVICE

CROSS-REFERENCE TO RELATED APPLICATIONS

This is a continuation-in-part of application Ser. No. 063,268, filed Aug. 2, 1979, now U.S. Pat. No. 4,296,751 and entitled "Surgical Device".

BACKGROUND OF THE INVENTION

The present invention, like the one in the related application, is concerned with a ligator device, i.e. with a forceps-like device which dispenses ligating clips and applies them to severed blood vessels and other small fluid ducts, to close the same.

However, although the device disclosed in the copending application works very well, it is relatively complicated in its constrcution and a simpler, less complicated construction is desirable.

SUMMARY OF THE INVENTION

It is a general object of the present invention to provide such a simpler, less complicated ligating device.

A more particular object of the invention is to provide an improved ligating device which is simple and uncomplicated in its construction, but is nevertheless wholly reliable in operation.

Still another object of the invention is to provide such an improved ligating device which can readily be made of disposable materials, so that it can be discarded when it has served its use.

In keeping with these objects, and with still others which will become apparent as the description proceeeds, one aspect of the invention resides in a ligating device which, briefly stated, may comprise a ligator device, comprising a pair of handles, a longitudinally movable center slide linked to the handles so as to move rearward when the handles are squeezed together, a pair of jaws each slidably connected to a front portion of the center slide and each having a fron end provided with an anvil and means connecting the jaws with the center slide for the anvils to move together when the handles are squeezed, and for the anvils to move apart when the handles are released.

The invention will hereafter be described with reference to an examplary embodiment. However, it should be understood that this is for purposes of explanation only and is not to be considered limiting of the invention in any sense.

BRIEF DESCRIPTION OF THE DRAWINGS

FIG. 1 is a top plan view of a ligator device embodying the present inventon;

FIG. 2 is a diagrammatic top plan view, partly broken away and with still other parts removed, of the same ligator device as in FIG. 1;

FIG. 3 is a section taken on line III—III of FIG. 2;

FIG. 4 is an exploded view, illustrating certain components of the device in FIGS. 1–3.

DESCRIPTION OF PREFERRED EMBODIMENTS

Figure 5:
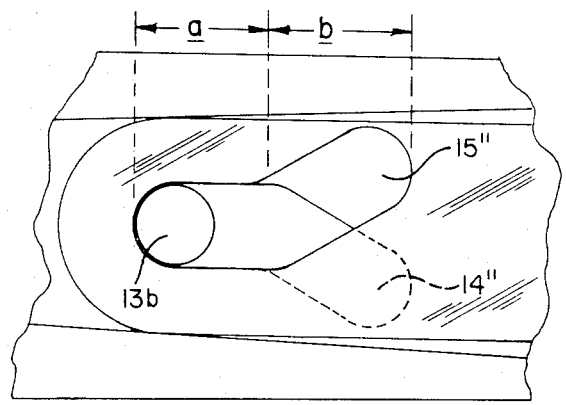
FIG. 5 is an enlarged plan view, illustrating a detail of the device.

FIG. 1 shows the device in a top plan view to provide in effect an overview and a general understanding. A pair of scissor-like handles 1, 2 are linked with one another (not shown) to operate a pair of jaws (not shown). Seated on top of the device is an elongated cartridge 3 which contains a series of ligating clips 4. These are seriatim dispensed to the jaws (every time the two handles are squeezed closer together) which then apply them to the blood vessel or the like.

The device is shown in more detail in FIGS. 2 and 3. Moved (i.e. squeezed-together or clip-setting) positions of the handles are indicated at 1a and 2a. The handles 1, 2 are connected by a two-part triangular link 5 whose ends are pivoted to the handles at 6 and whose other ends are pivoted to one another at 7. The handles 1, 2 themselves are pivoted to one another at 8. A spring 9 is secured at one end to a stud of the (broken-away) housing 10 and at the other end to a center slide 13 to retract the same. At the front end the device has anvils 11, 12 which squeeze the ligating clips to closed position (the magazine is omitted in this illustration).

As the section III—III (FIG. 3) shows, the cross-section of the jaws is so chosen that in the closed (clip-setting) position the jaws stabilize one another so that there can be no "wobbling" or similar movement. Most parts of the device, except for the spring 9, center slide 13 and link 5, and the anvils 11, 12, can be made of synthetic plastic material.

FIG. 4 is an exploded view, showing the jaws by themselves. Reference numeral 13 identifies the center slide (see also FIG. 2) to the rear of which the link 5 is pivoted at 7. It is bracketed top and bottom by a pair of jaws 14 and 15. Jaw 14 has a depending wall 14a at one side, jaw 15a a similar but upstanding wall 15a (both of these could be omitted) at the other side, so that between themselves they securely hold the center slide 13 against lateral break-out movement. The rear ends of jaws 14, 15 have holes 14', 15' and the center slide 13 is provided towards the rear with a longitudinally extending cut-out 13a. A pin 16 extends through cut-out 13a and holes 14', 15' to hold the pieces together.

About midway the jaws 14, 15 are formed with angled slots 14", 15" into which a pin 13b of center slide 13 extends. This is shown in more detail in FIG. 5 from where it will also be understood that the slot region a provides the necessary delay for retraction of the clips upstream of the one in the jaws (this is explained in detail in the copending application) whereas the region b provides the camming action for closing the jaws and setting the clip by the anvils 11, 12.

The invention has hereinbefore been described with reference to examplary embodiment. However, various modifications and changes will offer themselves to those skilled in the art and these are intended to be encompassed within the scope of the appended claims.

I claim:

1. A ligator device, comprising
   a pair of handles;
   a longitudinally movable center slide linked to said handles so as to move rearward when the handles are squeezed together;
   a pair of jaws each slidably connected to a front portion of said center slide and each having a front end provided with an anvil;
   means connecting said jaws to said center slide for said anvils to move together when said handles are squeezed and for said anvils to move apart when the handles are released;
   a cartridge with a supply of ligating clips; and means for retracting all except the respectively leading clip located between said anvils, in direction rearwardly away from said anvils prior to movement of said anvils together, said retracting means comprising a slot in one of said jaws and angled crosswise thereof in one direction, a slot in the other jaw and angled crosswise thereof in the opposite direction, and a pin integral with said front portion of said center slide and extending through said slots.

* * * * *